United States Patent [19]
Hrib

[11] Patent Number: 5,247,097
[45] Date of Patent: Sep. 21, 1993

[54] OXOLABDANES

[75] Inventor: Nicholas J. Hrib, Somerville, N.J.

[73] Assignee: Hoechst-Roussel Pharmaceuticals Incorporated, Somerville, N.J.

[21] Appl. No.: 889,585

[22] Filed: May 28, 1992

Related U.S. Application Data

[60] Division of Ser. No. 653,823, Feb. 11, 1991, Pat. No. 5,130,332, which is a continuation-in-part of Ser. No. 493,610, Mar. 15, 1990, abandoned, which is a division of Ser. No. 381,885, Jul. 19, 1989, Pat. No. 4,933,476, which is a division of Ser. No. 153,631, Feb. 8, 1988, Pat. No. 4,883,885, which is a division of Ser. No. 901,337, Aug. 28, 1986, Pat. No. 4,740,522.

[51] Int. Cl.$^5$ ............... C07D 327/10; C07D 311/92; C07F 7/02
[52] U.S. Cl. ............................ 549/4; 549/31; 549/214; 549/383; 549/389
[58] Field of Search ............ 549/389, 383, 214, 4, 549/31

[56] References Cited

U.S. PATENT DOCUMENTS

| | | | |
|---|---|---|---|
| 4,134,986 | 1/1979 | Bajwa. | |
| 4,517,200 | 5/1985 | Kreutner. | |
| 4,564,626 | 1/1986 | Kreutner. | |
| 4,578,399 | 3/1986 | Schorlemmer | 514/455 |
| 4,639,443 | 1/1987 | Kosley et al. | 514/222 |
| 4,639,446 | 1/1987 | Kosley | 549/389 |
| 4,677,103 | 6/1987 | Kosley | 549/31 |
| 4,724,238 | 2/1988 | Dohadwalla et al. | 549/389 |
| 4,751,224 | 6/1988 | Agarwal | 514/248 |
| 4,851,397 | 7/1989 | Kosley | 549/214 |
| 4,963,537 | 10/1990 | Kosley et al. | 549/389 |

FOREIGN PATENT DOCUMENTS

| | | |
|---|---|---|
| 0116713 | 8/1984 | European Pat. Off.. |
| 0126313 | 11/1984 | European Pat. Off.. |
| 0189801 | 8/1986 | European Pat. Off.. |
| 0191166 | 8/1986 | European Pat. Off.. |
| 0193132 | 9/1986 | European Pat. Off.. |
| 0212293 | 3/1987 | European Pat. Off.. |
| 0293814 | 12/1988 | European Pat. Off.. |
| 3346869 | 7/1984 | Fed. Rep. of Germany. |
| 3407514 | 9/1985 | Fed. Rep. of Germany. |
| 8503637 | 8/1985 | World Int. Prop. O.. |

Primary Examiner—C. Warren Ivy
Assistant Examiner—A. A. Owens
Attorney, Agent, or Firm—Raymond R. Wittekind

[57] ABSTRACT

Novel oxolabdanes, intermediates and processes for the preparation thereof, and methods for reducing intraocular pressure utilizing compounds or compositions thereof are disclosed.

8 Claims, No Drawings

OXOLABDANES

This is a division of application Ser. No. 07/653,823 filed Feb. 11, 1991, now U.S. Pat. No. 5,130,332 which is a continuation of application Ser. No. 07/493,610 filed Mar. 15, 1990, now abandoned, which is a divisional of application Ser. No. 07/381,885 filed Jul. 19, 1989, now U.S. Pat. No. 4,933,476 which is a divisional of application Ser. No. 07/153,631 filed on Feb. 8, 1988, now U.S. Pat. No. 4,883,885 which is a divisional of application Ser. No. 06/901,337 filed on Aug. 28, 1986 now U.S. Pat. No. 4,740,522.

The present invention relates to oxolabdanes. More particularly, the present invention relates to oxolabdanes of formula 1

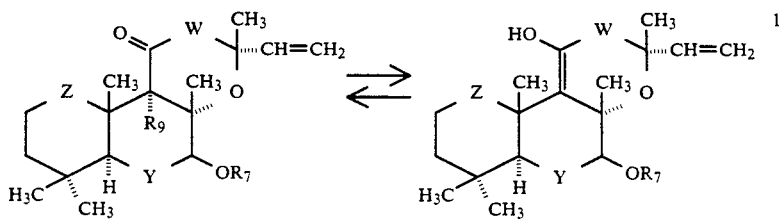

wherein:

(a) Z a group of the formula CO, a group of the formula $CHOR_1$ wherein $R_1$ is hydrogen, a group of the formula $R_2CO$ wherein $R_2$ is hydrogen or loweralkyl, or group of the formula $R_3R_4R_5Si$ wherein $R_3$, $R_4$ and $R_5$ are loweralkyl;

(b) is a group of the formula CO, a group of the formula $CHOR_6$ wherein $R_6$ is hydrogen, a group of the formula $R_8CO$ wherein $R_8$ is hydrogen, loweralkyl, $CH_3CHOH$, $HOCH_2CHOH$,

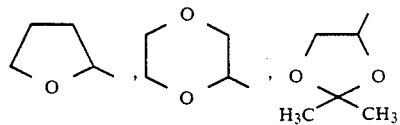

a group of the formula $R_{10}O(CH_2)_n$ wherein $R_{10}$ is hydrogen or loweralkyl and n is 2, 3 or 4;

(c) $R_7$ is hydrogen, a group of the formula $R_8CO$ wherein $R_8$ is hydrogen, loweralkyl, $CH_3CHOH$, $HOCH_2CHOH$,

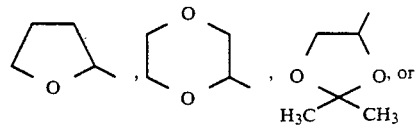

a group of the formula $R_{10}O(CH_2)_n$ wherein $R_{10}$ is hydrogen or loweralkyl and n is 2, 3 or 4;

(d) $R_9$ is hydrogen or a group of the formula $OR_{13}$ wherein $R_{13}$ is hydrogen;

(e) $R_6$ and $R_7$ taken together form a group of the formula CO or a group of the formula SO;

(f) $R_1$ and $R_{13}$ taken together form a group of the formula CO, a group of the formula SO, or a group of the formula $CHNR_{14}R_{15}$ wherein $R_{14}$ and $R_{15}$ are loweralkyl of 1 to 6 carbon atoms, with the proviso that the compound exists exclusively as the 11-keto tautomer when $R_9$ is $OR_{13}$ wherein $R_{13}$ is hydrogen, the optical and geometric isomers thereof, or a pharmaceutically acceptable acid addition salt thereof, which are useful for reducing intraocular pressure, alone or in combination with inert adjuvants.

Subgeneric to the oxolabdanes of the present invention are compounds of formula 1 wherein:

(a) W is a group of the formula CO; Z is a group of the formula $CHOR_1$ wherein $R_1$ is hydrogen or a group of the formula $R_2CO$ wherein $R_2$ is loweralkyl of 1 to 6 carbon atoms; and $R_9$ is a group of the formula $OR_{13}$ wherein $R_{13}$ is hydrogen;

(b) W is a group of the formula CO; Z is a group of the formula $CHOR_1$ wherein $R_1$ is hydrogen or a group of the formula $R_2CO$ wherein $R_2$ is loweralkyl of 1 to 6 carbon atoms; and $R_9$ is hydrogen;

(c) W is a group of the formula $CH_2$; Z is a group of the formula CO or a group of the formula $CHOR_1$ wherein $R_1$ is a group of the formula $R_2CO$ wherein $R_2$ is loweralkyl of 1 to 6 carbon atoms; Y is a group of the formula CO; and $R_9$ is hydrogen;

(d) $R_6$ and $R_7$ taken together form a group of the formula CO or a group of the formula SO;

(e) $R_1$ and $R_7$ taken together form a group of the formula CO or a group of the formula SO; and (f) $R_1$ and $R_{13}$ taken together form a group of the formula $CHNR_{14}R_{15}$.

The present invention also relates to compounds of formula

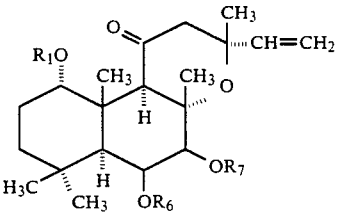

wherein $R_1$, $R_6$ and $R_7$ are each independently hydrogen or a group of the formula $R_{16}CO$ wherein $R_{16}$ is loweralkyl, or the optical and geomeric isomers thereof, which are useful for reducing intraocular pressure and as intermediates for the preparation of the oxolabdanes of the present invention.

As used through the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl, 3-hexyl, 4-heptyl, 2-octyl, and the like; the term "alkanol" refers to a compound formed by a combination of an alkyl group and a hydroxy radical. Examples of alkanols are methanol, ethanol, 1- and 2-propanol, 1,2-dimethylethanol, hexanol, octanol and the like. The term "alkanoic acid" refers to a compound formed by combination of a carboxyl group with a hydrogen atoms or alkyl group. Examples of alkanoic acids are formic acid, acetic acid, propanoic acid, 2,2-dimethylacetic acid, hexanoic acid, octanoic acid, and the like; the term "halogen" refers to a number of the family consisting of fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, and the like. The term "acyl" encompasses the term "alkanoyl" and refers to the radical derived from an organic acid by removal of the hydroxyl function. Examples of acyl radicals are tetrahydrofuroyl, 2,2-dimethyl-1,3-dioxolanoyl, 1,4-dioxolanoyl, methoxyacetoxy, and the like. The term "lower" as applied to any of the aforementioned groups refers to a group having a carbon skeleton containing up to and including 6 carbon atoms.

In the formulas presented herein the various substituents are illustrated as joined to the labdane nucleus by one of two notations: a solid line (—) indicating a substituent which is in the β-orientation (i.e., above the plane of the molecule) and a broken line (---) indicating a substituent which is in the α-orientation (i.e, below the plane of the molecule). The formulas have all been drawn to show the compounds in their absolute stereochemical configuration. Inasmuch as the starting materials having a labdane nucleus are naturally occurring or are derived from naturally occurring materials, they, as well as the final products, have a labdane nucleus existing in the single absolute configuration depicted herein. The processes of the present invention, however, are intended to apply as well to the synthesis of labdanes of the racemic series.

In addition to the optical centers of the labdane nucleus, the substituents thereon may also contain chiral centers contributing to the optical properties of the compounds of the present invention and providing a means for the resolution thereof by conventional methods, for example, by the use of optically active acids. A wavy line (~) connecting a group to a chiral center indicates that the stereochemistry of the center is unknown, i.e., the group may exist in any of the possible orientations. The present invention comprehends all optical isomers and racemic forms of the compounds of the present invention where such compounds have chiral centers in addition to those of the labdane nucleus.

The novel oxolabdanes of the present invention are synthesized by the processes illustrated in Reaction Schemes A, B, and C.

To prepare an 11,12-dioxolabdane 4, an 11-oxolabdane 2 wherein $R_1$ is hydrogen is oxidized to an 11,12-dioxo-9α-hydroxylabdane 3 which is reduced to 4. The oxidation is performed by treating 2 with selenium dioxide in a heteroaromatic solvent. Among heteroaromatic solvents there may be mentioned pyridine, picoline, lutidine and collidine. Pyridine is the preferred solvent. While the reaction temperature is not critical, the oxidation is preferably conducted at the reflux temperature of medium to promote a reasonable rate of reaction. The reduction is performed by treating 3, characterized by the presence of a 9α-hydroxy group, with zinc in an alkanoic acid. Included among alkanoic acids are acetic acid, propionic acid, and the like. Acetic acid is preferred. While the reduction temperature is not narrowly critical, it is generally performed at a temperature within the range of about 0° to about 50° C., a reduction temperature of about 25° C. being preferred. This process for the preparation of an 11,12-dioxolabdane 4 is preferred for the preparation of those compounds wherein $R_1$ and $R_6$ are hydrogen and $R_7$ is a group of the formula $R_8CO$ wherein $R_8$ is alkyl, and also provides access to 11,12-dioxo-9α-hydroxylabdanes 3 wherein $R_1$ and $R_9$ are hydroxy and $R_7$ is a group of the formula $R_8CO$ wherein $R_8$ is alkyl.

To prepare an 11,12-dioxolabdane of formula 4 wherein $R_1$ is $R_2CO$ and $R_6$ and $R_7$ are $R_8CO$ wherein $R_2$ and $R_8$ are alkyl, an 11-oxolabdane 2 wherein $R_1$, $R_6$, and $R_7$ are as above is oxidized with selenium dioxide in a heteroaromatic solvent such as pyridine under substantially the same condition as those described for the synthesis of 3 wherein $R_1$ and $R_6$ are hydroxy and $R_7$ is $R_8CO$ wherein $R_8$ is alkyl.

11,12-Dioxolabdanes 3 bearing hydroxyl and/or alkanoyloxy groups at the 1-, 6-, and 7-positions may be selectively alkanoylated or hydrolyzed by methods known in the art to provide hydroxy- and/or alkanoyloxy-11,12-dioxolabdanes 3, i.e., compounds of formula 3 wherein $R_1$ is hydrogen or $R_2CO$ wherein $R_2$ is alkyl and $R_6$ and $R_7$ are hydrogen or $R_8CO$ wherein $R_8$ is alkyl.

To prepare a 6β-alkanoyloxy-11,12-dioxolabdane 3 wherein $R_6$ is $R_8CO$ wherein $R_8$ is alkyl, a 7β-alkanoyloxy-11,12-dioxolabdane 4 wherein $R_7$ is $R_8CO$ wherein $R_8$ is alkyl may be rearranged by, for example, treatment with either sodium hydroxide in methanol or lithium bis(trimethylsilyl)amide in tetrahydrofuran.

To elaborate an 11,12-dioxolabdane 3 having a silyl group at the 1-position, i.e., a compound of formula 3 wherein $R_1$ is $R_3R_4R_5Si$ wherein $R_3$, $R_4$, and $R_5$ are alkyl, one may treat an 11,12-dioxolabdane 3 wherein $R_1$ is hydrogen with, for example, t-butyldimethylsilyl trifluoromethanesulfonate in triethylamine at a reaction temperature of about 25° C.

To introduce an acyl function at the 1-position of the labdane nucleus, i.e., to prepare an 11,12-dioxolabdane of formula 3 wherein $R_1$ is acyl, a 1-hydroxylabdane 3 wherein $R_1$ is hydrogen may be treated with an organic acid of formula 12

$$R_2CO_2H \qquad 12$$

wherein $R_2$ is as hereinbeforedescribed in dichloromethane in the presence of 1,3-dicyclohexylcarbodiimide and a catalyst such as 4-(N,N-dimethylamino)pyridine at a reaction temperature of about 25° C. To introduce an acyl function at the 6- or 7-positions of the labdane nucleus, i.e., to prepare an 11,12-dioxolabdane of formula 3 wherein $R_6$ and/or $R_7$ is acyl, a 6β,β-dihydroxylabdane 3 wherein $R_6$ or $R_7$ is hydrogen may be treated with an organic acid of formula 13

$$R_8CO_2H \qquad 13$$

wherein $R_8$ is as hereinbeforedescribed under conditions substantially similar to those employed for the introduction of an acyl function at the 1-position.

To introduce a 6β,β-sulfite or 6β,β-carbonate function into an 11,12-oxolabdane 3, i.e., to prepare a compound of formula 3 wherein $R_6$ and $R_7$ taken together form a group of the formula SO or a group of the formula CO, respectively, a 6β,β-dihydroxylabdane of formula 3 may be contacted with a compound of formula 14

$$HalXHal \qquad 14$$

wherein X is SO or CO and Hal is bromo or chloro, preferably chloro, in pyridine at a reaction temperature of about 0° C.

In addition, by condensing a 1α,9α-dihydroxy-11,12-dioxolabdane 3, i.e, a compound of formula 3 wherein $R_1$ and $R_{13}$ are hydrogen, with a halide 14 wherein X is SO or CO under the hereinbeforedescribed process conditions, one may obtain, respectively, a 1α,9α-sulfite or a 1α,9α-carbonate, i.e., compounds of formula 3 wherein $R_1$ and $R_{13}$ taken together form a group of the formula SO or a group of the formula CO, respectively.

To construct an 11,12-dioxolabdane 3 wherein $R_1$ and $R_{13}$ form a group of the formula $CHNR_{14}R_{15}$ wherein $R_{14}$ and $R_{15}$ are 3 loweralkyl, i.e., an 11,12-dioxolabdane-1α,9α-dihydroxylabdane is condensed with a formamide dialkylacetal of formula 15

$$(R_{17}O)_2CHNR_{14}R_{15} \qquad 15$$

wherein $R_{17}$ alkyl and $R_{14}$ and $R_{15}$ are as above neat or in the presence of dimethylformamide at a condensation temperature of about 45° to about 65° C.

By applying the aforedescribed alkanoylation, hydrolysis, rearrangement, silylation, acylation, sulfite and carbonate formation, and condensation reactions to an 11,12-dioxo-9α-hydroxylabdane, i.e., a compound of formula 3 wherein $R_{13}$ is hydrogen, and subsequently performing the aforementioned reduction, alkanoyloxy, hydroxy, silyl, acyl, sulfite, and carbonate derivatives of 4 may be prepared.

To furnish a 1,6,11-trioxolabd-14-ene 6 wherein $R_7$ is $R_8CO$ wherein $R_8$ is alkyl, a 1α,6β-dihydroxylabd-14-en-11-one 5 wherein $R_7$ is as above is oxidized with a benzeneseleninic anhydride of formula 16

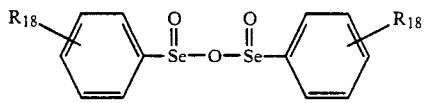

wherein $R_{18}$ is hydrogen, alkyl, alkoxy, halogen, nitro or trifluoromethyl in the presence of an alkali metal hydride and an aromatic solvent. Among alkali metal hydrides are lithium hydride, potassium hydride and sodium hydride. Among aromatic solvents are benzene, toluene, and xylene. Benzeneseleninic anhydride is the preferred oxidizing agent. Sodium hydride and toluene the preferred alkali metal hydride and reaction solvent. While the reaction temperature is not narrowly critical, it is preferred to conduct the oxidation at the reflux temperature of the reaction medium to assure a reasonable rate of reaction.

To modify the substituent at the 7-position of a compound of formula 6, a 7β-alkanoyloxylabd-14-en-1,6,11-trione 6 wherein $R_7$ is $R_8CO$ wherein $R_8$ is alkyl, may be hydrolyzed under conventional conditions employing, for example, sodium carbonate in methanol to provide a 7β-hydroxylabdane 6 wherein $R_7$ is hydrogen and then condensed with an organic acid 13, i.e, an substantially similar to those hereinbeforedescribed to provide compounds of formula 6 wherein $R_7$ is as described above.

Similarly, to prepare a 6,11-dioxolabd-14-ene 8 wherein $R_1$ and $R_7$ are, respectively, $R_2CO$ and $R_8CO$ wherein $R_2$ and $R_8$ are alkyl, a 6β-hydroxylabd-14-en-11-one 7 is oxidized with a benzeneseleninic anhydride 16 under essentially the same conditions utilized for the conversion of 5 to 6. The $C_1$- and $C_7$- alkanoyoxy groups of the 6,11-dioxolabdane 8, i.e., a compound of formula 8 wherein $R_2$ and $R_8$ are alkyl, may be hydrolyzed as discussed above to afford a 1α,7β-dihydroxylabd-14-en-6,11-dione 8 wherein $R_1$ and $R_7$ are hydrogen, which hydroxyl groups may be modified by condensation with a carboxylic acid of the formula $R_8CO_2H$ under reaction conditions also as discussed above.

The labdane starting material for the processes of the present invention are fabricated from readily available precursors. For example, 7β-acetoxy-1α,6β-dihydroxy-8,13-epoxylabd-14-en-11-one, i.e., the compound of formula 9 wherein $R_7$ is $R_8CO$ wherein $R_8$ is methyl, is rearranged by means of lithium bis(trimethylsilyl)amide in tetrahydrofuran to 6β-acetoxy-1α,7β-dihydroxy-8,13-epoxylabd-14-en-11-one, i.e., a compound of formula 10 wherein $R_6$ is $R_8CO$ wherein $R_8$ is methyl, which is aceylated by acetic anhydride to 8,13-epoxy-1α,6β,7β-triacetoxylabd-14-en-11-one 11, i.e., a compound of formula 11 wherein $R_1$ is $R_2CO$ and $R_6$ and $R_7$ are $R_8CO$ wherein $R_2$ and $R_8$ are methyl.

The labdanes of the present invention are useful in the treatment of elevated intraocular pressure by virtue of their ability to reduce intraocular pressure as determined by the method described by J. Caprioli, et al., Invest. Ophthalmol. Vis. Sci., 25, 268 (1984). The results of the determination express as percent decrease of outflow pressure is presented in the Table.

TABLE

| Compound | Concentration (%) | Decrease in Outflow Pressure (%) |
|---|---|---|
| 7β-acetoxy-8,13-epoxy-1α, 6β, 9α-trihydroxylabd-14-en-11,12-dione | 2 | 25.8 |
| 7β-acetoxy-8,13-epoxy-1α, 6β, 9α-trihydroxy-labd-14-en-11-one | 1.0 | 51 |
| | 0.1 | 23 |

Intraocular pressure reduction is achieved when the present labdanes are administered to a subject requiring such treatment as an effective topical dose of a 0.01 to 3.0% solution or suspension. A particularly effective amount is about 3 drops of a 1% preparation per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the invention include:

(1) 7β-acetoxy-6β,9α-dihydroxy-8,13-epoxy-1α-formyloxylabd-14-en-11,12-dione;

(2) 7β-acetoxy-1α-(t-butyldimethylsilyloxy)-6β,9α-dihydroxy-8,13-epoxylabd-14-en-11,12-dione;

(3) 1α,7β-diacetoxy-6β,9α-dihydroxy-8,13-epoxylabd-14-en-11,12-dione;

(4) 7β-acetoxy-1α,9β-dihydroxy-8,13-epoxy-6β-formyloxylabd-14-en-11,12-dione;

(5) 6β,7β-diacetoxy-1α,9α-dihydroxy-8,13-epoxylabd-14-en-11,12-dione;

(6) 8,13-epoxy-6β-[(2-hydroxypropionyl)oxy]-1α,7β,-9α-trihydroxylabd-14-en-11,12-dione;

(7) 8,13-epoxy-6β-[(2-tetrahydrofuroyl)oxy]-1α,7β,9α-trihydroxylabd-14-en-11,12-dione.

(8) 6β-[(1,4-dioxan-2-yl)carbonyloxy]-8,13-epoxy-1α,7β,9α-trihydroxylabd-14-en-11,12-dione;

(9) 6β-[(2,2-dimethyl-1,3-dioxolano-4-yl)carbonyloxy]-8,13-epoxy-1α,7β,9α-trihydroxylabd-14-en-11,12-dione;
(10) 8,13-epoxy-6β-(methoxyacetoxy)-1α,7β,9α-trihydroxylabd-14-en-11,12-dione;
(11) 8,13-epoxy-6β-[(2,3-dihydroxypropionyl)oxy]-1α,7β,9α-trihydroxylabd-14-en-11,12-dione;
(12) 8,13-epoxy-1α,6β,7β,9α-tetrahydroxylabd-14-en-11,12-dione;
(13) 8,13-epoxy-7β-formyloxy-1α,6β,9α-trihydroxylabad-14-en-11,12-dione;
(14) 8,13-epoxy-7β-[(2-hydroxypropionyl)oxy]-1α,6β,9α-trihydroxylabd-14-en-11,12-dione;
(15) 8,13-epoxy-7β-[(2-tetrahydrofuroyl)oxy]-1α,6β,9α-trihydroxylabd-14-en-11,12-dione;
(16) 7β-[(1,4-dioxan-2-yl)carbonyloxy]-8,13-epoxy-1α,6β,9α-trihydroxylabd-14-en-11,12-dione;
(17) 7β-[(2,2-dimethyl-1,3-dioxolano-4-yl)carbonyloxy)]-8,13-epoxy-1α,6β,9α-trihydroxylabd-14-en-11,12-dione;
(18) 8,13-epoxy-7β-(methoxyacetoxy)-1α,6β,9α-trihydroxylabd-14-en-11,12-dione;
(19) 8,13-epoxy-7β-[(2,3-dihydroxypropionyl)oxy)-1α,6β,9α-trihydroxylabd-4-en-11,12-dione;
(20) 7β-acetoxy-8,13-epoxy-1α,6β,9α-trihydroxylabd-14-en-11,12-dione-1,9-carbonate;
(21) 7β-acetoxy-8,13-epoxy-1α,6β,9α-trihydroxylabd-14-en-11,12-dione-1,9-sulfite;
(22) 1α-acetoxy-8,13-epoxy-1α,7β,9α-trihydroxylabad-14-en-11,12-dione-6,7-carbonate;
(23) 1α-acetoxy-8,13-epoxy-6β,7β,9α-trihydroxylabd-14-en-11,12-dione-6,7-sulfite; and
(24) 7β-acetoxy-8,13-epoxy-1α6β,9α-trihydroxylabd-14-en-11,12-dione-1,9-dimethylformamide acetal.

Effective amounts of the compounds of the present invention may be administered to a subject by any one of various methods, for example, orally as in capsules or tablets, parenterally in the form of sterile solutions or suspensions, in some cases intravenously in the form of sterile solutions, or suspensions, and topically in the form of solutions, suspension or ointments, and by aerosol spray. The labdanes of the present invention, while effective themselves, may be formulated and administered in the form of their pharmaceutically acceptable addition salts for purposes of increased solubility and the like.

Preferred pharmaceutically acceptable addition salts include salts of mineral acids for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, citric acid and the like.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.1–30 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example as coating. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purpose of parenteral or topical therapeutic administration, the active compounds of the invention may be incorporated into a solution, suspension, ointment or cream. These preparations should contain at least 0.01% of active compound, but may be varied between 0.5 and about 5% of the weight thereof. The amount of active compounds in such compositions is such that a suitable dosage will be obtained. Preferred compositions and preparations according to the present invention are prepared so that a parenteral dosage unit contains between 0.01 to 10 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylendiaminetetraacetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

The following examples are for illustrative purposes only and are not to be construed as limiting the invention. All temperatures are given in degrees Centigrade.

EXAMPLE 1

7β-Acetoxy-8,13-epoxy-1α,6β,9α-trihydroxylabd-14-en-11,12-dione

To a solution of 200 mg of 7β-acetoxy-8,13-epoxy-1α,6β-dihydroxylabd-14-en-11-one in 60 ml dry pyridine was added 300 mg of selenium dioxide. The mixture was heated to reflux with stirring under a Dri-Rite drying tube. After 18 hr, the mixture was cooled, diluted with 50 ml of ether and filtered. The solvent was removed in vacuo, the residue taken up in ether and filtered through silica. The filtrate was concentrated and the residue was recrystallized from ether-hexane to give 68 mg (32%) of product, mp 185°-187° C.

ANALYSIS: Calculated for $C_{22}H_{32}O_8$: 62.25%C: 7.59%H: Found: 61.92%C: 7.51%H.

EXAMPLE 2

7β-Acetoxy-8,13-epoxy1α,6β,11-trihydroxylabd-9(11),14-dien-12-one

To a stirred solution of 52 mg of 7β-acetoxy-8,13-epoxy-1α,6β,9α-trihydroxylabd-14-en-11,12-dione in 4 ml of glacial acetic acid was added in one portion 50 mg of zinc dust. The suspension was stirred at ambient temperature for 15 min, then diluted with 10 ml of water. The aqueous phase was thrice extracted with ether. The combined organic extracts were dried over anhydrous magnesium sulfate, filtered and the solvent removed in vacuo. The residue crystallized to give 42.2 mg (94%) of product, mp 89°-91°.

ANALYSIS: Calculated for $C_{22}H_{32}O_7$: 64.69%C: 7.90%H: Found: 64.76%C: 8.02%H.

EXAMPLE 3

8,13-Epoxy-1α,6β,7β-triacetoxy-11-hydroxylabd-9(11),14-dien-12-one

To a solution of 150 mg of 8,13-epoxy-1α,6β,7β-triacetoxylabd-14-en-11-one in 30 ml of pyridine was added 200 mg of selenium dioxide. The mixture was heated to reflux with stirring under a Dri-Rite drying tube. After 18 hr the mixture was cooled, diluted with 50 ml ether and filtered. The solvent was removed in vacuo and the residue taken up in ether and filtered through silica. The filtrate was concentrated to give 130.6 mg (84%) of product, mp 214°-216° (dec).

ANALYSIS: Calculated for $C_{26}H_{36}O_9$: 63.40%C: 7.37%H: Found: 63.17%C: 7.49%H.

EXAMPLE 4

7β-Acetoxy-8,13-epoxylabd-14-en-1,6,11-trione

To a solution of 200 mg of 7β-acetoxy-1α,6β-dihydroxy-8,13-epoxylabd-14-en-11-one in 60 ml of toluene was added first 480 mg of benzeneseleninic anhydride then 200 mg of sodium hydride (50% dispersion in oil). The mixture was heated to reflux with stirring under nitrogen. After 24 hr the mixture was cooled to ambient temperature, the solids were filtered and the solvent removed in vacuo. The residue was chromatographed on silica using 4:1 hexane/ethyl acetate eluent to provide 78.9 mg (40%) of product, mp 127°-129°.

ANALYSIS: Calculated for $C_{22}H_{30}O_6$: 67.67%C: 7.74%H: Found: 67.51%C: 7.95%H.

EXAMPLE 5

1α,7β-Diacetoxy-8,13-epoxylabd-14-en-6,11-dione

To a solution of 200 mg of 1α,7β-diacetoxy-8,13-epoxy-6β-hydroxylabd-14-en-11-one in 25 ml of dry toluene was added first 200 mg of benzene seleninic anhydride then 30 mg (97%) sodium hydride. The mixture was stirred and heated to reflux under a Dririte drying tube. After 18 hr, the mixture was cooled and filtered. The filtrate was concentrated, taken up in 9:1 hexane/ethyl acetate, and chromatographed on silica. Evaporation of the appropriate fractions afforded 93.6 mg (47%) of product, mp 163°-164°.

ANALYSIS: Calculated for $C_{24}H_{34}O_7$: 66.33%C: 7.88%H: Found 66.07%C: 7.71%H.

EXAMPLE 6

8,13-Epoxy-1α,6β,7β-triacetoxylabd-14-en-11-one

To a solution of 100 mg of 1α,7β-dihydroxy-8,13-epoxy-6β-acetoxylabd-14-en-11-one in 20 ml of dichloromethane and 1 ml of triethylamine, was added 1 ml of acetic anhydride. The solution was heated to reflux for 8.0 hr. It was then allowed to cool to room temperature, the volatiles were removed in vacuo, and the residue filtered through silica gel using 3:1 hexane/ethyl acetate eluent. The filtrate was concentrated to afford 102 mg (84%) of product.

ANALYSIS: Calculated for $C_{26}H_{38}O_8$: 65.25%C: 8.00%H: Found: 64.76%C: 7.87%H.

EXAMPLE 7

6β-Acetoxy-1α,7β-dihydroxy-8,13-epoxylabd-14-en-11-one

In 20 ml of dry tetrahydrofuran, 100 mg of 7β-acetoxy-1α,6β-dihydroxy-8,13-epoxylabd-14-en-11-one was dissolved with stirring under a nitrogen atmosphere. The solution was cooled to −78° (dry ice-acetone bath) and 0.79 ml of 1M solution of lithium bis(trimethylsilyl)amide in tetrahydrofuran was introduced. The mixture was stirred for 30 min at −78°. The solution was poured into water and extracted with ether. The combined organic extracts were dried over anhydrous magnesium sulfate, filtered, and concentrated in vacuo. This residue was recrystallized from hexane/ethyl acetate to give 79.8 mg (79.9%) of product.

ANALYSIS: Calculated for $C_{22}H_{34}O_6$: 66.98%C: 8.69%H: Found: 66.48%C: 8.68%H.

EXAMPLE 8

1α,7β-Diacetoxy-8,13-epoxy-6β-hydroxylabd-14-en-11-one

A solution of 1.0 g of 7β-acetoxy-1α,6β-dihydroxy-8,13-epoxylabd-14-en-11-one in 40 ml of triethylamine and 10 ml of acetic anhydride was heated to 90° with stirring under nitrogen. After 72 hr the mixture was cooled and the volatiles were removed in vacuo. The residue was taken up in ether and filtered through silica to give an oil that solidified. The solid was subjected to flash chromatography in silica using 9:1 hexane/ethyl acetate. The appropriate fractions were combined and concentrated to give 948 mg (87%) of product.

ANALYSIS: Calculated for $C_{24}H_{30}O_7$: 66.03%C: 8.31%H: Found: 66.10%C: 8.28%H.

REACTION SCHEME A
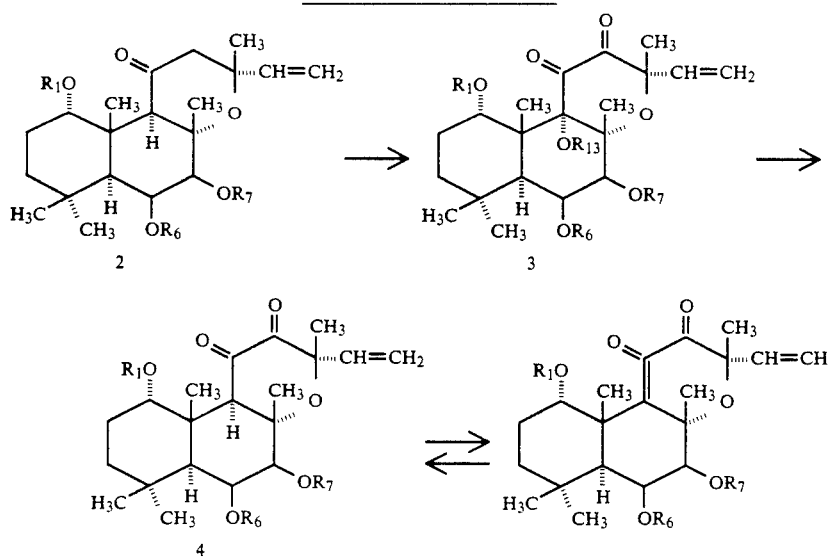
wherein $R_1$, $R_6$, $R_7$, and $R_{13}$ are as hereinbeforementioned.
REACTION SCHEME B
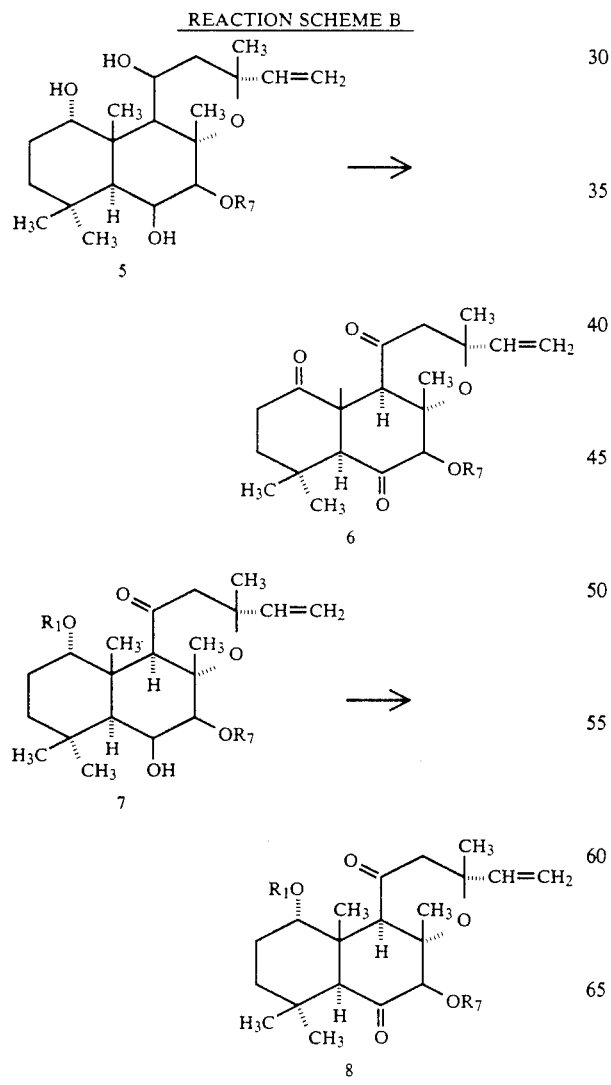
wherein $R_7$ is as hereinbeforedefined.
REACTION SCHEME C
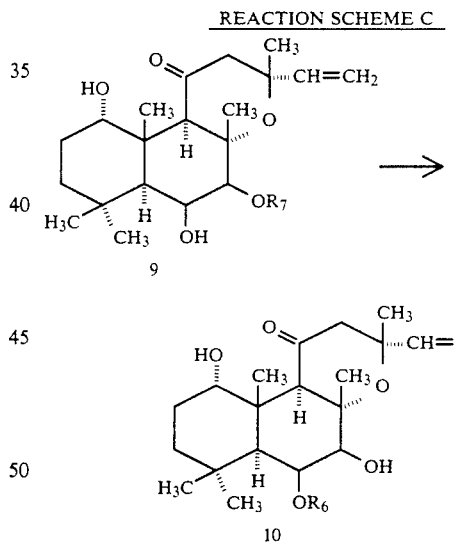
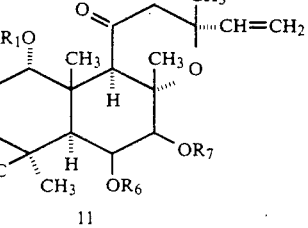
wherein $R_6$ and $R_7$ are as hereinbeforedefined.
I claim:
1. A process for the preparation of a compound of the formula

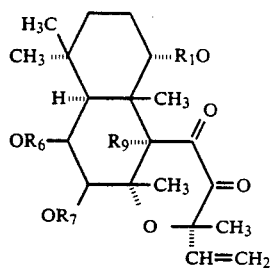

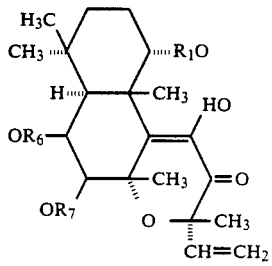

wherein:

(a) $R_1$ is hydrogen, a group of the formula $R_2CO$ wherein $R_2$ is hydrogen or loweralkyl of 1 to 6 carbon atoms, or a group of the formula $R_3R_4R_5Si$ wherein $R_3$, $R_4$ and $R_5$ are loweralkyl of 1 to 6 carbon atoms;

(b) $R_6$ and $R_7$ are independently hydrogen, a group of the formula $R_8CO$ wherein $R_8$ is hydrogen, loweralkyl of 1 to 6 carbon atoms, $CH_3CHOH$, $HOCH_2$-CHOH,

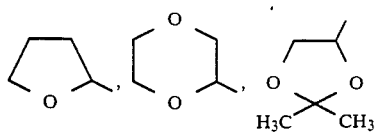

or a group of the formula $R_{10}O(CH_2)_n$ wherein $R_{10}$ is independently hydrogen or loweralkyl of 1 to 6 carbon atoms and n is 2, 3, or 4;

(c) $R_9$ is hydrogen;

(d) $R_6$ and $R_7$ taken together form a group of the formula CO or a group of the formula SO; or an optical or geometric isomer thereof which comprises contacting a compound of the formula

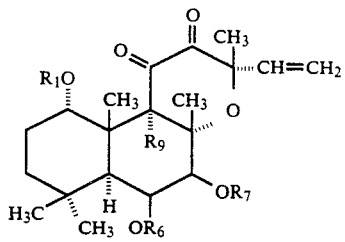

wherein $R_1$, $R_6$ and $R_7$ are as above and $R_9$ is $R_{13}O$ wherein $R_{13}$ is hydrogen with zinc in the presence of an alkanoic acid.

2. The process of claim 1 wherein the alkanoic acid is acetic acid.

3. A process for the preparation of a compound of the formula

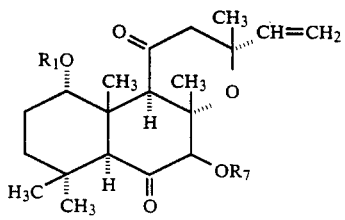

wherein $R_1$ and $R_7$ are groups of the formula $R_2CO$ and $R_8CO$, respectively, wherein $R_2$ and $R_8$ are loweralkyl of 1 to 6 carbon atoms which comprises contacting a compound of the formula

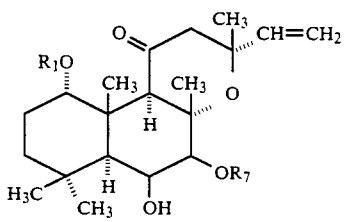

wherein $R_1$ and $R_7$ are as above with a compound of the formula

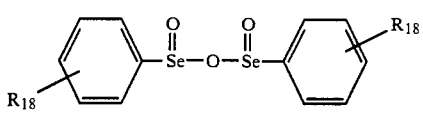

wherein $R_{18}$ is hydrogen, alkyl, alkoxy, halogen, nitro or trifluoromethyl in the presence of an alkali metal hydride.

4. The process of claim 3 wherein the alkali metal hydride is sodium hydride.

5. The process of claim 3 wherein $R_{18}$ is hydrogen.

6. The process of claim 3 wherein a solvent is employed.

7. The process of claim 6 wherein the solvent is an aromatic solvent.

8. The process of claim 7 wherein the aromatic solvent is toluene.

* * * * *